(12) United States Patent
Naiki

(10) Patent No.: US 10,891,636 B2
(45) Date of Patent: Jan. 12, 2021

(54) INFORMATION COLLECTION SYSTEM

(71) Applicant: Rohm Co., Ltd., Kyoto (JP)

(72) Inventor: Takashi Naiki, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 286 days.

(21) Appl. No.: 15/531,016

(22) PCT Filed: Aug. 3, 2015

(86) PCT No.: PCT/JP2015/071952
§ 371 (c)(1),
(2) Date: May 26, 2017

(87) PCT Pub. No.: WO2016/084426
PCT Pub. Date: Jun. 2, 2016

(65) Prior Publication Data
US 2017/0323311 A1     Nov. 9, 2017

(30) Foreign Application Priority Data

Nov. 28, 2014   (JP) ................................ 2014-241627

(51) Int. Cl.
*G06Q 30/02* (2012.01)
*G06K 7/10* (2006.01)
(Continued)

(52) U.S. Cl.
CPC ....... *G06Q 30/0201* (2013.01); *G01C 22/006* (2013.01); *G06K 7/10* (2013.01);
(Continued)

(58) Field of Classification Search
None
See application file for complete search history.

(56) References Cited

U.S. PATENT DOCUMENTS 6,008,546 A * 12/1999 Sage .................... G05D 1/0255
307/9.1
9,098,873 B2 * 8/2015 Geisner ................. G06Q 30/02
(Continued)

FOREIGN PATENT DOCUMENTS

JP    2000-357177 A    12/2000
JP    2006-309280 A    11/2006
(Continued)

OTHER PUBLICATIONS

Di Fan, Ying He, Xuyang Yao, Smart Shopping Cart, Spring 2012 (Year: 2012).*
(Continued)

*Primary Examiner* — Akosua Kyereme-Tuah
(74) *Attorney, Agent, or Firm* — Fish & Richardson P.C.

(57) ABSTRACT

An information collection system 1 has: a stand-alone-power-type transmitter 10 capable of moving together with a mobile entity (purchaser) A1, the transmitter 10 spontaneously and intermittently transmitting a transmitter ID at a timing corresponding to the distance of movement of the mobile entity A1; a plurality of receivers 20 provided in an area X to be monitored in which the mobile entity A1 can move freely, the receivers 20 receiving the transmitter ID transmitted from the transmitter 10 present in the vicinity of the area X; and a server 30 for managing the transmitter ID, the position information (receiver ID) of the receiver 20 that receives the transmitter ID, and a time of day at which the receiver ID is received, in association with each other.

7 Claims, 8 Drawing Sheets

(51) Int. Cl.
*G06K 19/07* (2006.01)
*G06Q 10/08* (2012.01)
*G01C 22/00* (2006.01)
*G06Q 20/20* (2012.01)
*A61B 5/11* (2006.01)
*A61B 5/00* (2006.01)

(52) U.S. Cl.
CPC ......... *G06K 7/10415* (2013.01); *G06K 19/07* (2013.01); *G06K 19/0707* (2013.01); *G06K 19/0716* (2013.01); *G06K 19/0723* (2013.01); *G06Q 10/087* (2013.01); *G06Q 10/0833* (2013.01); *G06Q 20/20* (2013.01); *G06Q 30/02* (2013.01); *A61B 5/0002* (2013.01); *A61B 5/1113* (2013.01); *A61B 5/1117* (2013.01)

(56) References Cited

U.S. PATENT DOCUMENTS

| | | | | |
|---|---|---|---|---|
| 2001/0027423 | A1* | 10/2001 | Clonts | G06Q 30/0601 705/26.8 |
| 2005/0200476 | A1* | 9/2005 | Forr | G06Q 30/0267 340/539.13 |
| 2005/0285461 | A1* | 12/2005 | Kitamura | H02K 7/1846 310/67 A |
| 2007/0076593 | A1* | 4/2007 | Sakurai | B60W 50/0205 370/219 |
| 2009/0273444 | A1* | 11/2009 | Brown | H04Q 9/00 340/10.1 |
| 2010/0298657 | A1* | 11/2010 | McCombie | A61B 5/021 600/301 |
| 2012/0150488 | A1* | 6/2012 | Kamiyama | G01C 22/006 702/160 |
| 2012/0249325 | A1* | 10/2012 | Christopher | G06Q 30/02 340/539.13 |
| 2012/0326641 | A1* | 12/2012 | Sakai | H02J 3/32 318/400.3 |
| 2013/0009783 | A1* | 1/2013 | Tran | A61B 5/0402 340/669 |
| 2013/0096869 | A1 | 4/2013 | Yuzawa et al. | |
| 2013/0293355 | A1* | 11/2013 | Christopher | G06Q 30/0241 340/10.1 |
| 2014/0062352 | A1* | 3/2014 | Wang | A01D 34/78 318/139 |
| 2014/0132728 | A1* | 5/2014 | Verano | G06K 9/00771 348/46 |
| 2016/0048905 | A1* | 2/2016 | Yuan | G06Q 30/0635 705/26.81 |

FOREIGN PATENT DOCUMENTS

| | | |
|---|---|---|
| JP | 2008-193595 A | 8/2008 |
| JP | 2009-003872 A | 1/2009 |
| JP | 2009-210516 A | 9/2009 |
| JP | 2012-065232 A | 3/2012 |
| JP | 2013-084170 A | 5/2013 |
| JP | 5580469 B1 | 8/2014 |

OTHER PUBLICATIONS

Japanese Patent Office, International Search Report for corresponding International Patent Application PCT/JP2015/071952 dated Oct. 27, 2015 (with translation), 4 pages.

* cited by examiner

FIG. 5

|  | TXID | SN | RXID | RTC |
|---|---|---|---|---|
| \<Y2\> | 001 | 0123 | 01 | 10:00:15 |
| \<Y3\> | 001 | 0124 | 02 | 10:00:30 |
| \<Y4\> | 001 | 0125 | 03 | 10:01:50 |
| \<Y6\> | 001 | 0127 | 04 | 10:02:30 |
| \<Y7\> | 001 | 0128 | 05 | 10:02:45 |
| \<Y8\> | 001 | 0129 | 06 | 10:04:05 |
|  | ⋮ | ⋮ | ⋮ | ⋮ |

INFORMATION COLLECTION SYSTEM

TECHNICAL FIELD

The present invention relates to an information collecting system.

BACKGROUND ART

Patent Documents 1 and 2 identified below disclose information collecting systems that collect location information as to shoppers in a store by reading IDs of IC tags fitted to shopping carts or shopping baskets with a plurality of IC tag readers provided in the store and managing the respective IDs of the IC tags and the IC tag readers and the times at which they were read in an associated manner.

LIST OF CITATIONS

Patent Literature

Patent Document 1: JP-A-2000-357177
Patent Document 2: JP-A-2006-309280

SUMMARY OF THE INVENTION

Technical Problem

Inconveniently, however, the conventional information collecting systems mentioned above assume the use of externally-powered transmitters (passive tags) as the IC tags, and give no consideration to a system design that uses self-powered transmitters (active tags) (such as a design of a transmitter that can prevent collision without requiring a complicated mediating process).

In view of the above problem encountered by the present inventor, an object of the invention discloses herein is to provide an information collecting system that uses a self-powered transmitter.

Means for Solving the Problem

According to what is disclosed herein, an information collecting system includes: a self-powered transmitter that is movable together with a mobile body and that intermittently transmits a transmitter ID spontaneously with timing correlated to the amount of movement of the mobile body; a plurality of receivers that are provided in a monitoring target area in which the mobile body can move freely and that receive a transmitter ID transmitted from a transmitter present nearby; and a server that manages the transmitter ID, location information of a receiver that received the transmitter ID, and a reception time of the transmitter ID in an associated manner (a first configuration).

In the information collecting system of the first configuration described above, the transmitter may include: an electric generator that converts a kinetic energy into an electric energy; an electric storage that stores the electric energy generated by the electric generator; and a transmission circuit that transmits the transmitter ID by being supplied with the electric energy each time a predetermined amount of electric energy is stored in the electric storage (a second configuration).

In the information collecting system of the first configuration described above, the transmitter may include: a revolution counter that counts the number of revolutions of a caster; and a transmission circuit that transmits the transmitter ID each time the number of revolutions of the caster reaches a predetermined value (a third configuration).

In the information collecting system of the first configuration described above, the transmitter may include: a pedometer that counts the number of steps; and a transmission circuit that transmits the transmitter ID each time the number of steps reaches a predetermined value (a fourth configuration).

In the information collecting system of any one of the first to fourth configurations described above, the transmitter may transmit, together with the transmitter ID, a serial number that is incremented each time the transmitter ID is transmitted (a fifth configuration).

In the information collecting system of any one of the first to fifth configurations described above, the server may manage, together with the transmitter ID, also the reception strength at the receiver in an associated manner (a sixth configuration).

In the information collecting system of any one of the first to sixth configurations described above, the mobile body may be a shopper, and the monitoring target area may be a store or a market (a seventh configuration).

In the information collecting system of the seventh configuration described above, the transmitter may be fitted to a shopping cart, a shopping basket, or a store admission permit that the shopper carries with him or her (an eighth configuration).

In the information collecting system of the seventh or eighth configuration described above, there may be further provided a cash register that transmits shopping information of the shopper and the transmitter ID in an associated manner to the server (a ninth configuration).

In the information collecting system of any one of the first to sixth configurations described above, the mobile body may be a patient, a person in need of nursing care, a school child, a kindergarten child, a domestic animal, or a domestic fowl, and the monitoring target area may be a hospital, a nursing-care facility, a school, a kindergarten, a nursery school, or a rearing facility (a tenth configuration).

Advantageous Effects of the Invention

According to the invention disclosed herein, it is possible to provide an information collecting system that uses a self-powered transmitter.

BRIEF DESCRIPTION OF DRAWINGS

FIG. 5 is a data table showing one example of a database managed by a server 30;

DESCRIPTION OF EMBODIMENTS

Figure 1:
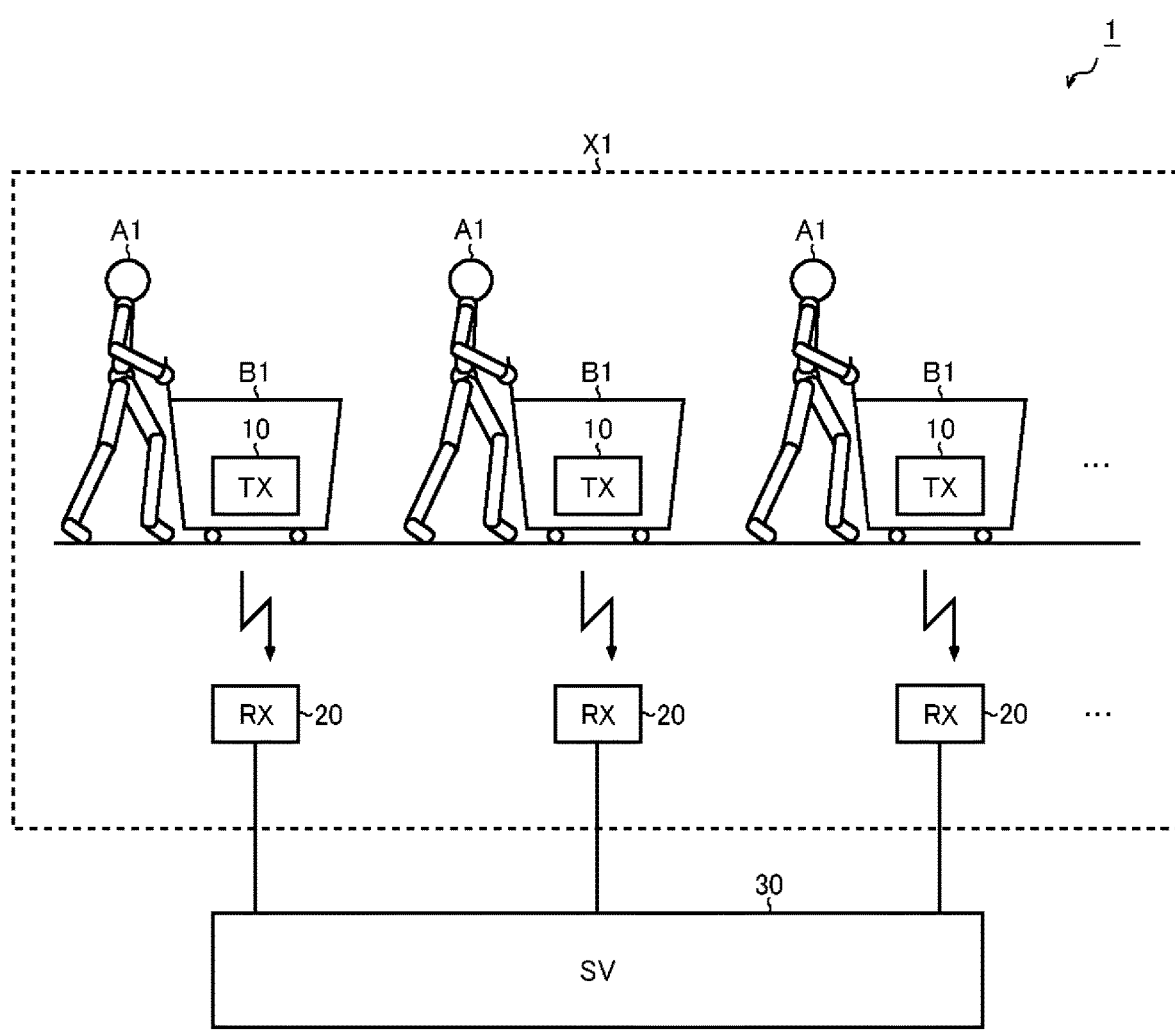
FIG. 1 is a conceptual diagram showing one configuration example of an information collecting system.

FIG. 1 is a conceptual diagram showing one configuration example of an information collecting system. The information collecting system 1 of this configuration example includes at least one transmitter 10 (usually a plurality of transmitters), a plurality of receivers 20, and a server 30.

The transmitter 10 is fitted to a shopping cart B1 (an example of a piece of store equipment) operated by a shopper A1 (an example of a mobile body); thus, as the shopper A1 walks around, the shopping cart B1 moves inside a store X1 (an example of a monitoring target area). The transmitter 10 is of a self-powered type (a so-called active tag) that can operated without being supplied with electric power from outside. One distinctive operation of the transmitter 10 is that it intermittently transmits a transmitter ID, which is unique to each transmitter, spontaneously with timing correlated to the amount of movement of the shopper A1. The technical significance of such transmission operation will be described in detail later.

The receivers 20 are installed at scattered places in the store X1, in which the shopper A1 can walk around freely, and are reception antennas for receiving transmitter IDs transmitted asynchronously from transmitters A1 present nearby. The receivers 20 are connected to the server 30 on a wired or wireless basis, and sends received transmitter IDs to the server 30. The receivers 20 are assigned receiver IDs unique to them respectively, and these IDs are managed by the server 30 in a centralized manner.

The server 30 manages, in an associated manner, transmitter IDs transmitted from transmitters 10, location information (coordinate data inside the store X1 associated with receiver IDs) as to the receivers 20 that have received the transmitter IDs, and the reception times (RTC (real-time clock) data) of the transmitter IDs. The server 30 may be installed in the store X1, or in a centralized control facility that comprehensively manages a plurality of stores X1. The contents of the database managed by the server 30 will be described later by way of specific examples.

<Transmitter>

Figure 2:
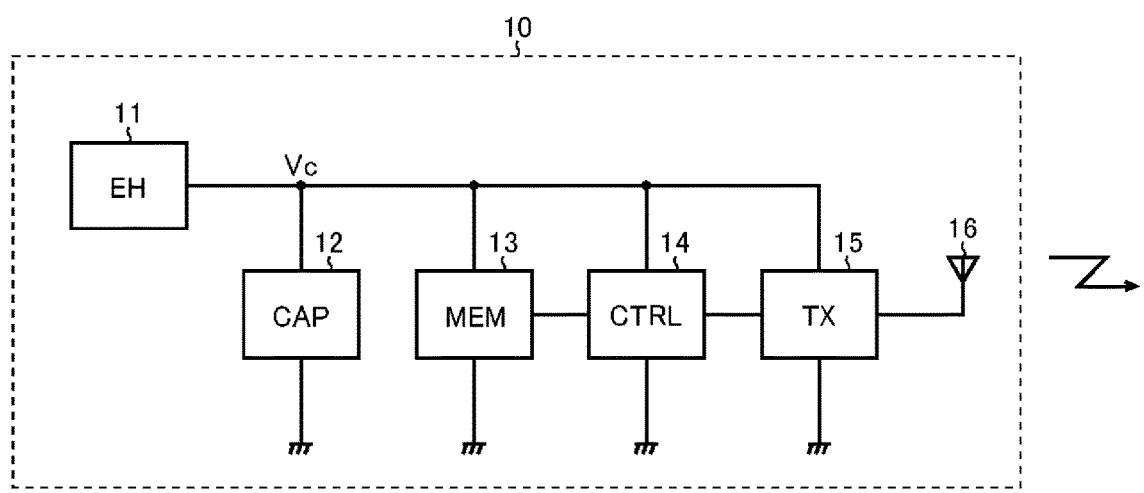
FIG. 2 is a block diagram showing one configuration example of a transmitter 10.

FIG. 2 is a block diagram showing one configuration example of the transmitter 10. The transmitter 10 of this configuration example includes an electric generator 11, an electric storage 12, a memory 13, a controller 14, a transmission circuit 15, and an antenna 16.

The power generator 11 converts the kinetic energy resulting from the walking of the shopper A1 into an electric energy. Usable as the electric generator 11 is, for example, a commutator electric generator that generates electric power on the basis of the rotating movement of a caster provided on the shopping cart B1, or a MEMS (microelectromechanical system) vibration electric generator that generates electric power on the basis of the vibration applied to the transmitter 10. Providing such an electric generator 11 eliminates the need for replacement or charging of a battery. It is thus possible to realize maintenance-free operation comparable with that realized by use of an externally-powered transmitter 10 (a so-called passive tag).

The electric storage 12 stores the electric energy generated by the electric generator 11, and feeds the charged voltage Vc to relevant parts in the transmitter 10. Usable as the electric storage 12 is a capacitor, a lithium-ion secondary cell, or the like.

The memory 13 stores transmitter IDs unique to transmitters 10 on a non-volatile basis. Usable as the memory 13 is an EEPROM (electrically erasable programmable read-only memory), an OTPROM (one-time programmable ROM), a flash memory, or the like.

The controller 14 operates by being supplied with the charged voltage Vc each time it reaches a predetermined operable voltage Vdrv, and carries out control such as the control of the access to the memory 13 (control for reading a transmitter ID) and the control of the driving of the transmission circuit 15 (control for modulating an antenna driving signal according to the transmitter ID).

The transmission circuit 15 operates by being supplied with the charged voltage Vc each time it reaches the predetermined operable voltage Vdrv, and carries out a process for transmitting the transmitter ID by driving the antenna 16 according to the antenna driving signal fed from the controller 14.

The antenna 16 converts an electric signal modulated according to the transmitter ID into a radio wave, and radiates it out of the transmitter 1.

<Transmission Timing>

Figure 3:
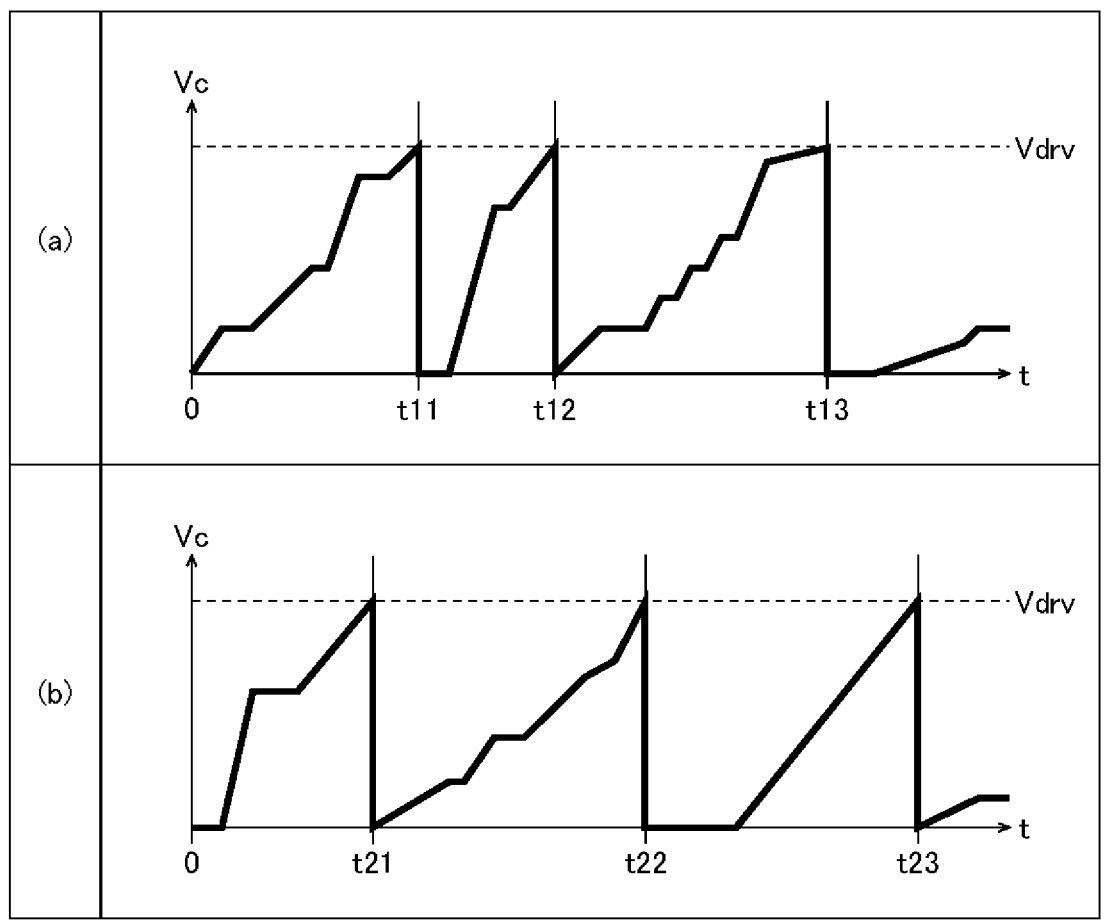
FIGS. 3A and 3B are timing charts each showing a relationship between the amount of movement of a shopper and the timing of transmission.

FIGS. 3A and 3B are timing charts showing the relationship between the amount of movement of the shopper (hence the amount of electric power generated by the electric generator 11) and the timing of transmission, depicting how the charged voltage Vc varies with time in transmitters 10 carried by different shoppers A1a and A1b respectively.

The shoppers A1a and A1b move around freely in the store X1 to shop for the desired goods. As a matter of course, how fast each shopper walks and when he or she pauses vary unpredictably. That is, the speed of the charging of the charged voltage Vc resulting from a shopper A1 walking varies constantly according to how individual shoppers A1a and A1b move around in the store X1.

Thus, the time required for the charged voltage Vc to reach the operable voltage Vdry varies greatly, so that transmitter IDs are transmitted with random timing. For example, in the example shown in FIG. 3A, the transmitter ID is transmitted at times t11, t12, and t13; in contrast, in the example shown in FIG. 3B, the transmitter ID is transmitted at times t21, t22, and t23.

By intermittently transmitting transmitter IDs unique to transmitters spontaneously with timing correlated to the amounts of movement of shoppers A1 in this way, it is possible to prevent collision without requiring a complicated mediating process.

Moreover, with the above configuration, unless the charged voltage Vc reaches the operable voltage Vdrv, the controller 14 and the transmission circuit 15 cannot operate. This makes it possible to determine the timing of transmission of transmitter IDs without requiring separate enabling control or the like. It is thus possible to configure the transmitter 10 in an extremely simple configuration. In addition, when a shopper A1 is standing still, no transmission operation takes place, and this helps avoid unnecessary congestion of communication.

What has been described above is not meant to limit how to control transmission timing in accordance with the amount of movement of the shopper A1. Instead, for example, a revolution counter that counts the number of revolutions of a caster on the shopping cart B1 may be provided additionally, in which case the transmission circuit 15 can be controlled so as to transmit the transmitter ID each time the number of revolutions of the caster reaches a predetermined value. In a case where the transmitter 10 is fitted not to the shopping cart B1 but to a shopping basket B1' (see FIG. 7B), a pedometer that counts the number of steps of the shopper A1 may be provided additionally, in which case the transmission circuit 15 can be controlled so as to transmit the transmitter ID each time the number of steps reaches a predetermined value.

Although these configurations require the additional provision of a revolution counter or a pedometer, adopting one of them makes it possible to separate the movement of the shopper A1 from the operation for generating electric power. It is then possible to use as the electric generator 11 a photoelectric conversion element (photoelectric cell), or to replace the electric generator 11 with a dry-cell battery or a rechargeable battery, and this helps diversify the system design.

In the illustrated examples, each time the transmitter ID is transmitted, the charged voltage Vc is consumed completely. Instead, in a case where the controller 14 needs to be in operation on a continuous basis, the operable voltage Vdry can be raised so that, even after the transmitter ID is transmitted, a sufficient charged voltage Vc is left to allow the controller 14 to operate.

<Shopping Behavior Analysis>

Figure 4:
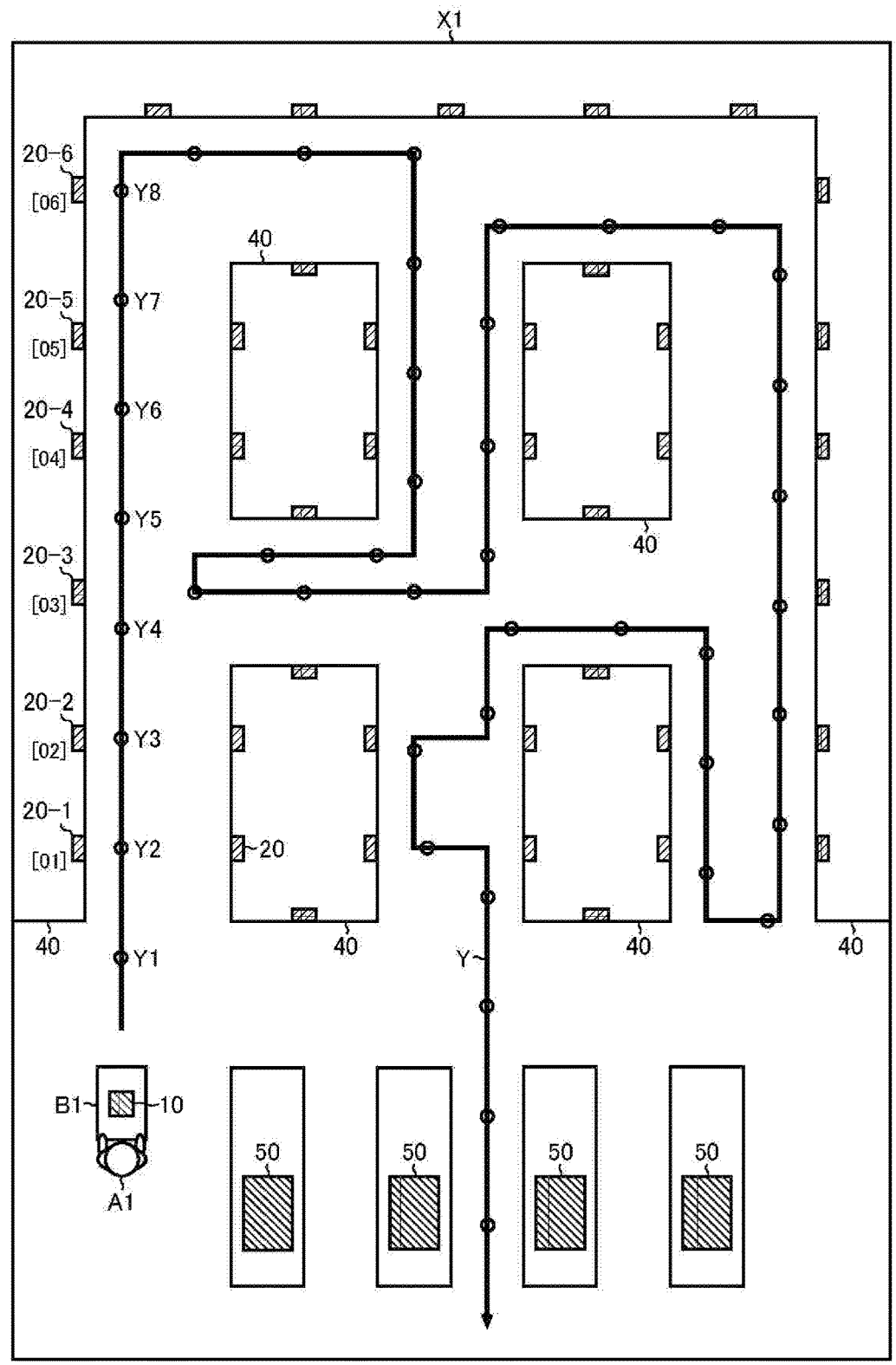
FIG. 4 is a schematic plan view which is a floor map of a store X1.

FIG. 4 is a schematic plan view which is a floor map of the store X1. In a selling space (for example, one for foodstuffs) of the store X1, a plurality of display racks 40 are installed. A shopper A1 can move freely across passage ways provided among the display racks 40. FIG. 4 depicts how a shopper A1, pushing a shopping cart B1, follows a path Y until he or she eventually pays for the purchase at a cash register of a POS (point-of-sale) system.

The shopping cart B1 is fitted with a transmitter 10 that intermittently transmits a transmitter ID unique to it spontaneous with timing correlated to the amount of movement of the shopper A1. The store X1 is furnished with a plurality of receivers 20 that receive transmitter IDs transmitted from transmitters A1 present nearby and that then send them to a server 30 (not shown in FIG. 4). In FIG. 4, for the sake of convenience of illustration, the display racks 40 are fitted with the receivers 20. This, however, is not meant to limit where to fit the receivers 20; the receivers 20 may be fitted to the floor or the ceiling.

Each circle on the path Y represents a transmission location at which the transmitter 10 transmitted the transmitter ID. As mentioned above, each time the charged voltage Vc reaches the operable voltage Vdry (that is, each time the shopper A1 moves a predetermined distance), the transmitter 10 transmits the transmitter ID. Accordingly, the ID transmission locations on the path Y are located approximately at equal intervals.

Now, with focus on the ID transmission locations Y1 to Y8 immediately after the shopper A1 entered the selling space, the contents of a databased managed by the server 30 will be described specifically.

FIG. 5 is a data table showing one example of the database managed by the server 30. In the database, transmitter IDs (TXID), serial numbers (SN), receiver IDs (RXID), and reception times (RTC) are associated with each other. The symbols <Y2>to <Y8>outside the table indicate that the shopper A1 (transmitter 10) is located at the ID transmission locations Y2 to Y8, respectively, in FIG. 4.

A transmitter ID (TXID) is terminal identification data (in FIG. 5, "001") that is transmitted from the transmitter 10 intermittently.

A serial number SN is the count of transmission instances that goes incremented by one each time the transmitter ID is transmitted, and is transmitted together with the transmitter ID (TXID) from the transmitter 10. The serial number SN can be incremented in the controller 14 in the transmitter 10. The serial number SN is not reset to an initial value when the shopper A1 starts or ends shopping around. That is, even after the shopper A1 has checked out at the POS cash register 50 and put away the shopping cart B1, the serial number SN is left unchanged from the last count. This configuration helps build a simpler information collecting system. The technical significance of adding serial numbers SN will be described later by way of specific examples.

A receiver ID (RXID) is terminal identification data that is unique to every receiver 20, and is managed by the server 30 in a centralized manner. The server 30 has, in a separate file, a location database in which receiver IDs and location information as to receivers 20 (data of coordinates inside the store X1) are associated together. Thus, when the path of the shopper A1 is analyzed on the server 30, reference is made not only to the database shown in FIG. 5 but, based on receiver IDs, also to the location database just mentioned.

A reception time (RTC) is time data as to the time at which a transmitter ID (TXID) transmitted from a transmitter 10 is received by a receiver 20.

In the following description, it is assumed that the receivers 20-1 to 20-6 arranged on the leftmost display racks 40 are assigned receiver IDs (RXID) "01" to "06" respectively. Now, with respect to the example of the movement of the shopper A1 indicated as the path Y, the contents of the database managed by the server 30 and how it is analyzed will be described specifically.

At ID transmission location Y1, the transmitter 10 transmits the transmitter ID (001) and the serial number SN (for example, 0122), but there is no receiver 20 present nearby that can receive them. Thus, no information is stored in the database of the server 30.

At ID transmission location Y2, the transmitter 10 transmits the transmitter ID (001) and the serial number SN (for example, 0123), and these are received by the receiver 20-1 present nearby. Thus, in the database of the server 30 is stored the following set of associated data: TXID (001), SN (0123), RXID (01), and reception time (10:00:15).

At ID transmission location Y3, the transmitter 10 transmits the transmitter ID (001) and the serial number SN (for example, 0124), and these are received by the receiver 20-2 present nearby. Thus, in the database of the server 30 is stored the following set of associated data: TXID (001), SN (0124), RXID (02), and reception time (10:00:30).

At ID transmission location Y4, the transmitter 10 transmits the transmitter ID (001) and the serial number SN (for example, 0125), and these are received by the receiver 20-3 present nearby. Thus, in the database of the server 30 is stored the following set of associated data: TXID (001), SN (0125), RXID (03), and reception time (10:01:50).

At ID transmission location Y5, the transmitter 10 transmits the transmitter ID (001) and the serial number SN (for example, 0126), but these are received by none of the receivers 20 due to some communication failure (such as collision). Thus, no information is stored in the database of the server 30.

At ID transmission location Y6, the transmitter 10 transmits the transmitter ID (001) and the serial number SN (for example, 0127), and these are received by the receiver 20-4 present nearby. Thus, in the database of the server 30 is stored the following set of associated data: TXID (001), SN (0127), RXID (04), and reception time (10:02:30).

At ID transmission location Y7, the transmitter 10 transmits the transmitter ID (001) and the serial number SN (for example, 0128), and these are received by the receiver 20-5 present nearby. Thus, in the database of the server 30 is stored the following set of associated data: TXID (001), SN (0128), RXID (05), and reception time (10:02:45).

At ID transmission location Y8, the transmitter 10 transmits the transmitter ID (001) and the serial number SN (for example, 0129), and these are received by the receiver 20-5 present nearby. Thus, in the database of the server 30 is stored the following set of associated data: TXID (001), SN (0129), RXID (06), and reception time (10:04:05).

The shopping behavior of the shopper A1 as seen from an analysis of the contents of the database presented thus far will now be described. First, by chronologically tracing the series of receiver IDs (more specifically, the location information as to those receivers which are associated with the receiver IDs), it is possible to know the path Y taken by the shopper A1 (for example, to know that, after entering the selling space in the store X1, the shopper A1 advanced along the leftmost display rack 40 in FIG. 4 toward the back of the selling space).

Moreover, based on the differences among the series of reception times, it is possible to know the movement speed of the shopper A1. For example, from the reception times at ID transmission locations Y2 to Y4 respectively, it is seen that, while the shopper A1 took 15 seconds to move from around the receiver 20-1 to around the receiver 20-2, he or she took 1 minute 20 seconds to move from around the receiver 20-2 to around the receiver 20-3. This tells that the shopper A1 passed by goods displayed between the receivers 20-1 and 20-2 without showing much interest but paused at goods displayed between the receivers 20-2 and 20-3, possibly showing interest to them.

Paying attention to ID transmission locations Y4 to Y6 allows one to see that one serial number SN is skipped. Adding serial numbers SN to transmitter IDs (TXID) in this way makes it possible, even if communication fails for some cause, to complement the contents of the database (in the illustrated example, the coordinates of ID transmission location Y5 at which communication failed, and the reception time plausible if the transmitter ID had been received properly). Moreover, if the ID transmission location Y5 can be estimated, it is possible to promptly investigate and remove the cause of failed communication (failure or misplacement of a receiver 20, or the like).

When the shopper A1 eventually pays for the purchase, the POS cash register 50 sends to the server 30 purchase information as to the shopper A1 (segment information such as goods bought, sex, and age group) in association with the transmitter ID of the transmitter 10 fitted to the shopping cart B1.

In the information collecting system 1 built as described above, the server 30 can manage the previously-described database as to the path Y of a shopper A1 in a manner linked with purchase information as to the shopper A1. Thus, it is possible to investigate, without human assistance, a series of shopping activities such as what path the shopper A1 took, where he or she stayed and how long, and what he or she eventually bought. The results of the investigation can be used in a variety of store improvement efforts, as in determining the quantities of goods to be procured and the range of goods to be offered, in changing how goods are to be displayed, and in optimizing the layout and widths of passage ways.

<Precise Location Detection>

Figure 6:
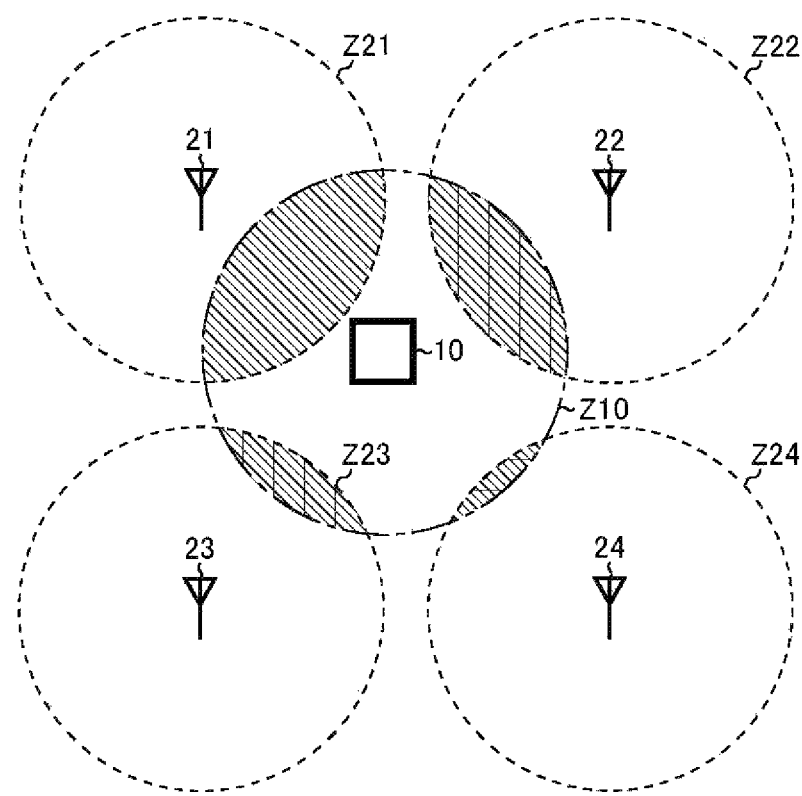
FIG. 6 is a conceptual diagram showing one example of a method for location detection based on reception strength.

FIG. 6 is a conceptual diagram showing one example of a method for detecting a location based on signal reception strength. In the illustrate example, it is assumed that there are four receivers 21 to 24 present around a transmitter and that the receivers 21 to 24 receive the transmitter ID with different reception strengths.

In FIG. 6, to visually illustrate differences in reception strength, the radio-wave reach range of the transmitter 10 and the reception ranges Z21 to Z24 of the receivers 21 to 24 are indicated by broken lines, the overlapping areas (hatched areas) between them representing reception strengths. It will be observed that, in the illustrated example, the receiver 21 exhibits the highest reception strength, the receivers 22 and 23 exhibit the next highest reception strength, and the receiver 24 exhibits the lowest reception strength.

By letting a plurality of receivers 21 to 24 receive the transmitter ID transmitted from a transmitter 10 in this way, it is possible, based on their combinations and the ratio of their respective reception strengths, to estimate the relative distances between the transmitter 10 and the receivers 21 to 24. Thus, by letting server 30 manage the transmitter ID in association also with the reception strengths at the receivers 21 to 24, it is possible to acquire more precise location information as to the shopper A1 (transmitter 10).

When an information collecting system is introduced into a store X1, adopting a location detection method based on reception strength is considered to be a preferred choice. When such a method is adopted, the transmitter ID transmitted from a transmitter 10 reaches a plurality of receivers 20. Accordingly, in response to a single transmission operation by the transmitter 10, a plurality of (for example, three) receiver units 20 succeed in a reception operation. As a result, for the same transmitter ID and the same serial number SN, different receiver IDs and different reception strength data corresponding to a plurality of (for example, three) receivers are recorded respectively in association at the same time (or approximately at the same time).

In that case, it is preferable that the record data stored in the server 30 be in the form of records with variable lengths, that is, in a form like: "time stamp", "transmitter ID", "serial number SN", "first receiver ID", "first reception strength", "second receiver ID", "second reception strength", . . . "n-th receiver ID", "n-th reception strength", <End of Record>.

When such record data is analyzed on a server 30 or the like, by use of the location information as to the individual receivers stored in a separate database and their respective reception strengths, it is possible to find the location (coordinates) of the transmitter based on the relative distances from the receivers to the transmitter by a method like a three-point method.

However, in a store or the like, for example, due to goods on the shelves being frequently replaced, the relationship between the relative distance to a transmitter and the reception strength at each receiver is not always constant but depends on the situation. As a solution to this problem, it is preferable to perform calibration. For example, a signal is forcibly transmitted from a fixed point (such as on a passage way) of which the coordinates are previously known, and the reception strength at each receiver is recorded. This is performed for a plurality of fixed points one after another. Then, the results can be used as compensation values in the server 30.

<Modified Examples>

Figure 7:
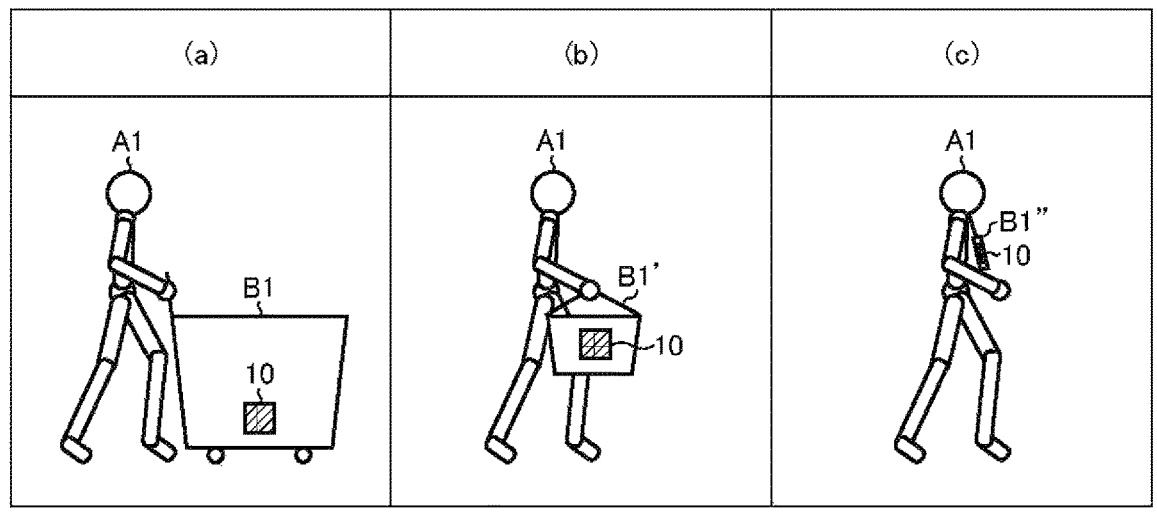
FIGS. 7A to 7C are diagrams showing variations of pieces of store equipment to which a transmitter 10 can be fitted.

FIGS. 7A to 7C are diagram showing variations of pieces of store equipment to which the transmitter 10 can be fitted. In FIGS. 7A, 7B, and 7C, the transmitter 10 is fitted to a shopping cart B1, a shopping bag B1', and a store admission permit B1", respectively, as items that a shopper A1 is highly likely to carry with him or her in a store X1. By fitting the transmitter 10 to such pieces of store equipment, it is possible to analyze the shopping behavior of the shopper A1 without giving him or her an impression of "being under constant monitoring".

Although, in the description above, an indoor floor of a store X1 is assumed to be the monitoring target area in which to monitor the shopping behavior of a shopper A1, this is not meant to limit the monitoring target area; it may be an entire market (such as a flea market site or a shopping area) where goods are marketed, irrespective of indoor or outdoor.

The information collecting system 1 can not only be used as a marketing tool, but can also be applied widely as a means for collecting location information as to a mobile body that moves freely in a monitoring target area. To follow is a brief description of such variations.

Figure 8:
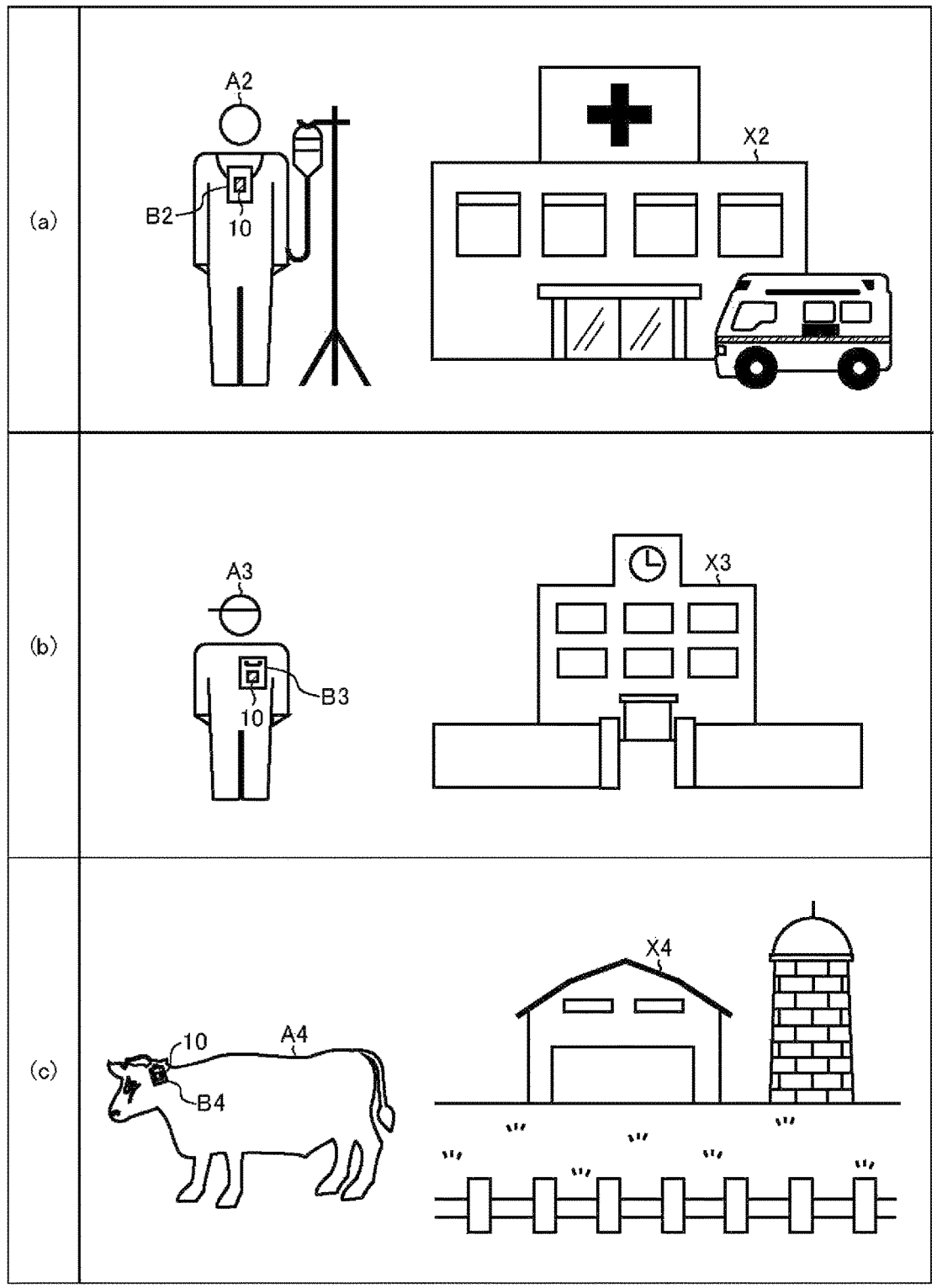
FIGS. 8A to 8C are diagrams showing variations of mobile bodies and monitoring target areas.

FIGS. 8A to 8C are diagrams showing variations of the mobile body and the monitoring target area. FIG. 8A shows a patient locating system where the mobile body is a patent A2 and the monitoring target area is a hospital X2. In building a system like this, it is preferable that the transmitter 10 be fitted to a patient tag B2 or the like that the patent A2 wears all the time. The patent A2 may instead be a person who requires nursing care, and the hospital X2 may instead be a nursing-care facility. A patient or person in need of nursing care can fall inadvertently and lie unnoticed in the absence of a doctor, a nurse, or a care person. With this in mind, in a case where the transmitter 10 has a stand-alone power supply that can generate spare electric power, the transmitter 10 may be provided with a posture sensor so that the sensing result (whether or not the wearer is lying) transmitted together with the transmitter ID is monitored on the server 30 all the time.

FIG. 8B shows a school-child locating system where the mobile body is a school child A3 and the monitoring target area is a school X3. In building a system like this, it is preferable that the transmitter 10 be fitted to a name tag B3 or the like that the school child A3 wears all the time. The school child A3 may instead be a kindergarten child, and the school X3 may instead be a kindergarten or a nursery school.

FIG. 8C show shows a domestic-animal locating system where the mobile body is a domestic animal A4 and the monitoring target area is a rearing facility X4. In building a system like this, it is preferable that the transmitter 10 be fitted to an ear tag B4 or the like that the domestic animal A4 wears all the time. Instead, the transmitter 10 may be implanted in the body of the domestic animal A4. The domestic animal A4 may instead be a domestic fowl.

<Other Modifications>

The various technical features disclosed herein may be implemented in any other manner than specifically described by way of embodiments above, and allows for many modifications within the scope of the technical ingenuity of the invention. That is, the embodiments described above should be considered to be in every aspect illustrative and not restrictive, and the technical scope of the present invention should be understood to be defined not by the description of embodiments given above but by the appended claims and to encompasses any modifications in the sense and scope equivalent to those of the claims.

INDUSTRIAL APPLICABILITY

Information collecting systems according to the present invention find applications as, for example, marketing tools for grasping or analyzing the traveled paths and the shopping behavior of shoppers in a store.

LIST OF REFERENCE SIGNS 1 information collecting system
10 transmitter
11 electric generator
12 electric storage
13 memory
14 controller
15 transmission circuit
16 antenna
20, 20-1 to 20-6, 21 to 24 receiver
30 server
40 display rack
50 POS cash register
A1 shopper
A2 patent
A3 school child
A4 domestic animal
B1 shopping cart
B1' shopping basket
B1" store admission permit
B2 patient tag
B3 name tag
B4 ear tag
X1 store
X2 hospital
X3 school
X4 rearing facility
Y path
Y1 to Y8 ID transmission location
Z10 radio-wave reach range
Z21 reception range

The invention claimed is:

1. An information collecting system, comprising:
a plurality of transmitters of a self-powered type, each transmitter being fitted to a respective shopping cart, a shopping basket, or an admission permit carried by a respective shopper who can move about in a store or a market, each transmitter being operable to transmit intermittently a respective transmitter ID, unique to the respective transmitter, spontaneously with random timing each time the shopper moves a predetermined distance;
a plurality of receivers provided at scattered places in the store or the market, the receivers operable to receive the transmitter ID transmitted from one of the transmitters located nearby;
a register that associates shopping information of the shopper with the transmitter ID; and
a server that manages the transmitter ID, location information of a receiver that received the transmitter ID, a reception time of the transmitter ID, and the shopping information of the shopper in an associated manner, the server thereby operable to investigate a series of shopping activities including what path the shopper took, where the shopper stayed and how long, and what the shopper bought, the server operable to output results of the investigation,
wherein each of the transmitters includes:
an electric generator configured to convert a kinetic energy, resulting from movement of the shopper about the store or market, into an electric energy;
an electric storage configured to store the electric energy generated by the electric generator; and
a transmission circuit configured to be supplied with the electric energy, and to transmit the transmitter ID, each time a predetermined amount of electric energy is stored in the electric storage, wherein the transmission circuit transmits the transmitter ID by being supplied with a charged voltage stored in the electric storage each time the charged voltage reaches a predetermined operable voltage of the transmission circuit, and wherein, the system is configured such that, even though there are multiple ones of the transmitters in the store or the market, each particular one of the transmitters is configured to prevent collision by intermittently transmitting the transmitter ID, which is unique to the particular transmitter, spontaneously with timing correlated to amounts of movement of shoppers.

2. The information collecting system according to claim 1, wherein each of the transmitters further includes:

a revolution counter configured to count a number of revolutions of a caster, wherein the transmission circuit transmits the transmitter ID each time the number of revolutions of the caster reaches a predetermined value.

3. The information collecting system according to claim 1, wherein each of the transmitters further includes:

a pedometer that counts a number of steps, wherein the transmission circuit transmits the transmitter ID each time the number of steps reaches a predetermined value.

4. The information collecting system according claim 1, wherein each respective one of the transmitters is operable to transmit, together with the transmitter ID, a serial number that is incremented each time the transmitter ID is transmitted.

5. The information collecting system according to claim 1, wherein the server manages, together with the transmitter ID, a reception strength at a respective one of the receivers in an associated manner.

6. The information collecting system according to claim 1, wherein the electric generator is a commutator electric generator that generates electric power on the basis of the rotating movement of a caster.

7. The information collecting system according to claim 1, wherein the electric generator is a MEMS (micro-electromechanical system) vibration electric generator that generates electric power on the basis of the vibration applied to the transmitter.

* * * * *